United States Patent
Freed

(10) Patent No.: US 9,278,048 B2
(45) Date of Patent: Mar. 8, 2016

(54) PHARMACEUTICAL PRODUCT AND METHOD OF USE

(75) Inventor: Simon Freed, Hillsborough, NJ (US)

(73) Assignees: BAXTER INTERNATIONAL, INC., Deerfield, IL (US); BAXTER HEALTHCARE SA, Glattpark (Opfikon) (CH)

( * ) Notice: Subject to any disclaimer, the term of this patent is extended or adjusted under 35 U.S.C. 154(b) by 562 days.

(21) Appl. No.: 12/436,401

(22) Filed: May 6, 2009

(65) Prior Publication Data

US 2010/0286648 A1    Nov. 11, 2010

(51) Int. Cl.
*A61J 1/00* (2006.01)
*B65D 23/02* (2006.01)
(Continued)

(52) U.S. Cl.
CPC . *A61J 1/00* (2013.01); *A61M 16/00* (2013.01); *A61M 16/104* (2013.01); *A61M 16/18* (2013.01); *A61M 16/183* (2013.01); *B65D 1/0215* (2013.01); *A61M 2205/6045* (2013.01); *F17C 2203/0604* (2013.01); *F17C 2203/0607* (2013.01); *F17C 2203/0612* (2013.01); *F17C 2203/0619* (2013.01); *F17C 2203/0634* (2013.01); *F17C 2203/0636* (2013.01); *F17C 2221/00* (2013.01)

(58) Field of Classification Search
CPC ....... A61J 1/00; A61J 2001/00; A61J 1/1412; A61J 2001/1468; B65D 25/14; B65D 85/84; A61M 16/18; A61M 16/183; A61M 15/0028; A61M 16/10; A61M 16/104; A61M 16/186; F17C 1/14; F17C 2203/0619; F17C 2203/0646; F17C 2203/0648; F17C 2223/0153; F17C 2223/033; F17C 2203/06; F17C 2203/0602; F17C 2203/0604; F17C 2203/0607; F17C 2203/0612; F17C 2203/0634; F17C 2203/0636; F17C 2221/00
USPC ........ 604/890.1, 23, 24, 48, 500; 128/200.24, 128/203.12, 204.17, 204.18
See application file for complete search history.

(56) References Cited

U.S. PATENT DOCUMENTS

| | | | |
|---|---|---|---|
| 2,720,203 | A | 10/1955 | Burns et al. |
| 3,997,694 | A | 12/1976 | Wu |

(Continued)

FOREIGN PATENT DOCUMENTS

| | | |
|---|---|---|
| EP | 0642992 | 3/1995 |
| JP | H01119265 | 5/1989 |

(Continued)

OTHER PUBLICATIONS

Datex-Ohmeda, Inc. Tec 7 Vaporizer User's Reference Manual. Accessed May 19, 2015. http://www.frankshospitalworkshop.com/equipment/documents/anaesthesia/service_manuals/Datex-Ohmeda_Tec7_-_Service_manual.pdf.*

(Continued)

*Primary Examiner* — Adam Marcetich
(74) *Attorney, Agent, or Firm* — Marshall, Gerstein & Borun LLP

(57) ABSTRACT

A pharmaceutical product includes a container. The container, in turn, includes a receptacle having a wall including a layer of nickel or nickel alloy, the layer facing an interior of the receptacle. The product also includes a halogenated anesthetic selected from the group consisting of sevoflurane, desflurane, isoflurane, enflurane, methoxyflurane and halothane disposed within the container.

20 Claims, 1 Drawing Sheet

(51) Int. Cl.
*A61M 16/10* (2006.01)
*A61M 16/18* (2006.01)
*A61M 16/00* (2006.01)
*B65D 1/02* (2006.01)

(56) References Cited

U.S. PATENT DOCUMENTS

| | | | | |
|---|---|---|---|---|
| 4,225,051 | A | * | 9/1980 | Faudou et al. ............ 220/590 |
| 4,250,334 | A | | 2/1981 | Coon et al. |
| 4,867,212 | A | | 9/1989 | Mohr et al. |
| 4,927,038 | A | * | 5/1990 | Roebuck ................ 220/590 |
| 5,062,999 | A | * | 11/1991 | Wallroth et al. ........... 261/39.1 |
| 5,451,258 | A | * | 9/1995 | Hillman et al. ............ 118/715 |
| 5,474,112 | A | * | 12/1995 | Carola ..................... 141/7 |
| 5,505,236 | A | | 4/1996 | Grabenkort et al. |
| 5,617,906 | A | | 4/1997 | Braatz et al. |
| 5,645,052 | A | * | 7/1997 | Kersey .................. 128/203.26 |
| 5,679,576 | A | | 10/1997 | Kawai et al. |
| 5,990,176 | A | | 11/1999 | Bieniarz et al. |
| 6,008,273 | A | | 12/1999 | Leibelt et al. |
| 6,074,668 | A | | 6/2000 | Flament-Garcia et al. |
| 6,083,514 | A | | 7/2000 | Chang et al. |
| 6,162,443 | A | | 12/2000 | Flament-Garcia et al. |
| 6,200,692 | B1 | * | 3/2001 | Tamura et al. ............. 428/629 |
| 6,234,352 | B1 | * | 5/2001 | Richard et al. ............. 222/95 |
| 6,253,762 | B1 | | 7/2001 | Britto |
| 6,315,985 | B1 | | 11/2001 | Wu et al. |
| 6,558,679 | B2 | | 5/2003 | Flament-Garcia et al. |
| 6,596,260 | B1 | | 7/2003 | Brugger et al. |
| 2001/0000729 | A1 | | 5/2001 | Flament-Garcia et al. |
| 2002/0050142 | A1 | * | 5/2002 | Wang et al. ................ 62/48.1 |
| 2002/0068767 | A1 | | 6/2002 | Rudzinski et al. |
| 2003/0141210 | A1 | | 7/2003 | Yanke et al. |
| 2003/0150446 | A1 | * | 8/2003 | Patel et al. ............. 128/200.14 |
| 2004/0250814 | A1 | * | 12/2004 | Post et al. ............. 128/203.12 |
| 2006/0144735 | A1 | * | 7/2006 | Baker ..................... 206/438 |
| 2007/0175905 | A1 | * | 8/2007 | Torres et al. ............. 220/586 |
| 2008/0000239 | A1 | * | 1/2008 | Timm et al. ............... 62/48.1 |
| 2008/0087283 | A1 | | 4/2008 | Cromack et al. |
| 2008/0173651 | A1 | * | 7/2008 | Ping ....................... 220/581 |
| 2008/0319202 | A1 | * | 12/2008 | Gin et al. ................ 548/300.1 |
| 2009/0107980 | A1 | * | 4/2009 | Andel et al. .............. 219/443.1 |
| 2009/0275785 | A1 | * | 11/2009 | Jones et al. ............... 568/682 |

FOREIGN PATENT DOCUMENTS

| | | |
|---|---|---|
| JP | H02291870 A | 12/1990 |
| JP | H06506846 A | 8/1994 |
| WO | WO-92/19303 A1 | 11/1992 |
| WO | WO96/32151 | 10/1996 |
| WO | WO97/09034 | 3/1997 |
| WO | WO98/40083 | 9/1998 |
| WO | WO99/34762 | 7/1999 |

OTHER PUBLICATIONS bottle—Dictionary Definition : Vocabulary.com. http://www.vocabulary.com/dictionary/bottle. Accessed Tue Oct. 27, 2015.*
bottle Meaning in the Cambridge English Dictionary. http://dictionary.cambridge.org/dictionary/english/bottle. Accessed Tue Oct. 27, 2015.*
Instructional Manual, EZ-6000-LINGAF Smart Flow Rodent Anesthesia System. Revised Oct. 2010. Accessed Apr. 2, 2015,. http://biosupport.licor.com/docs/SFManual.pdf.*
Kharasch; Evan D. Sevoflurane: The Challenges of Safe Formulation. Anesthesia Patient Safety Foundation Newsletter. vol. 22, No. 3, 2007. http://www.apsf.org/newsletters/html/2007/fall/03_sevoflurane.htm. Accessed Apr. 2, 2015.*
International Search Report and Written Opinion from corresponding International Application No. PCT/US2010/033903, dated Jul. 21, 2010 (8 pages).
Product Data Sheet, HOBA Internal Lining for Aerosol Cans 7407P (Jan. 1995) (1 page).
Safety Data Sheet, HOBA Lining 7407P (Jan. 1986) (1 page).
Correspondence between Monobloc USA and HOBA re 7407P (Dec. 17, 1986 and Jan. 20, 1987) (4 pages).
Examination Report of Prof. Nehring regarding HOBA 7407P (Aug. 12, 1982) (4 pages).
"Suprane (desflurane, USP)", 19 pp., retrieved from the Internet at: <http://dailymed.nim.nih.gov/dailymed/archives/fdaDrugInfo.cfm?archiveid=1008> (Feb. 1, 2009).

* cited by examiner

PHARMACEUTICAL PRODUCT AND METHOD OF USE

BACKGROUND

This patent is directed to a pharmaceutical product and method of use thereof, and in particular to an pharmaceutical product and method of use thereof for halogenated anesthetics.

It is well known to use machines, known as vaporizers, to convert anesthetics from a liquid form to a gaseous form that may be administered to a patient. The liquid anesthetic is typically stored in a bottle-type container. In use, the container is mated with a port on the vaporizer, and the liquid is transferred from an interior chamber of the container to a reservoir in the vaporizer. The liquid anesthetic is then vaporized and mixed with oxygen (and optionally other gases). The gaseous mixture may then be administered to the patient.

A number of different materials have been used to manufacture the container for use with such anesthetics.

Glass has been the traditional material of choice. Of course, glass presents certain challenges. Glass requires careful handling to avoid breakage, and when breakage does occur, product is lost and injury may occur. Additionally, U.S. Pat. No. 5,990,176 theorizes that certain halogenated inhalation anesthetics may react with components of the glass, causing the anesthetic to degrade. In particular, it is hypothesized that the aluminum oxides in the glass act as Lewis acids in the reaction that degrades the anesthetics.

In the alternative, certain plastics have been suggested for use in containers for storing halogenated anesthetics, such as sevoflurane. For example, U.S. Pat. No. 4,250,334 illustrates use of "Kel-F" plastic ("Kel-F" understood to be the trade name for polychlorotrifluoroethylene) to make a container for holding sevoflurane. U.S. Pat. No. 5,679,576 illustrates a container lined with polytetrafluoroethylene (PTFE) for holding sevoflurane. Similarly, the following patents illustrate plastic containers for sevoflurane: U.S. Pat. No. 6,074,668 (polyethylene napthalate); U.S. Pat. No. 6,083,514 (polymethylpentene); U.S. Pat. No. 6,162,443 (polypropylene, polyethylene and ionomeric resins); and U.S. Pat. No. 6,558,679. U.S. Pat. No. 5,505,236 also teaches the use of thermoplastic containers with liquid inhalation agents.

While plastic containers are less likely to break than glass containers, the containers are still susceptible to breakage under common use conditions. Moreover, many plastics tend to be vapor permeable, which may allow the inhalation anesthetic to escape the container over time. Vapor permeability also permits ambient vapors to enter the container, leading to possible contamination and/or change in the water content of the formulation. For that matter, inhalation anesthetics have strong organic solvent properties, and thus could cause the plastic to dissolve and/or to react, leading to measurable impurities in the inhalation anesthetic. Further, plastic containers are subject to deformation when exposed to elevated temperatures, which temperatures may be required during processing and treatment of the containers.

As a still further alternative, some have suggested use of metal containers. For example, U.S. Pat. No. 5,990,176 describes containers for sevoflurane made of stainless steel, glass or plastic for holding sevoflurane. A more recent discovery has been the use of aluminum to make containers for anesthetics such as sevoflurane, desflurane, isoflurane, enflurane, methoxyflurane and halothane. In particular, it has been suggested that aluminum containers be used, either unlined or lined with an enamel or a lacquer, which enamel or lacquer may include an epoxy-phenolic resin. See U.S. Publ. No. 2002/0068767.

On the other hand, it has been suggested that certain metals would not be acceptable for use in a container for anesthetics, and in particular halogenated anesthetics. See U.S. Publ. No. 2008/0087283. In particular, it is stated that degradation of sevoflurane has been observed in glass containers, and that the degradation is believed to be activated by trace amounts of Lewis acids present in the container. While aluminum oxide is identified in U.S. Publ. No. 2008/0087283 as one source for Lewis acids, it is stated therein that there are other "oxidizing" metals that would similarly provide Lewis acids. In particular, nickel and nickel alloys are identified as exemplary oxidizing metals.

As set forth in more detail below, the present disclosure sets forth an improved system embodying advantageous alternatives to the conventional systems and methods discussed above.

SUMMARY

In one aspect, a pharmaceutical product includes a container. The container, in turn, includes a receptacle having a wall including a layer of nickel or nickel alloy, the layer facing an interior of the receptacle. The product also includes a halogenated anesthetic selected from the group consisting of sevoflurane, desflurane, isoflurane, enflurane, methoxyflurane and halothane disposed within the container.

According to another aspect, a method of using of a pharmaceutical product may include obtaining a container including a receptacle having a wall including a layer of nickel or nickel alloy, the layer facing an interior of the receptacle. The method may also include filling the container with a halogenated anesthetic selected from the group consisting of sevoflurane, desflurane, isoflurane, enflurane, methoxyflurane, and halothane.

Additional aspects of the disclosure are defined by the claims of this patent.

BRIEF DESCRIPTION OF THE DRAWINGS

It is believed that the disclosure will be more fully understood from the following description taken in conjunction with the accompanying drawings. Some of the figures may have been simplified by the omission of selected elements for the purpose of more clearly showing other elements. Such omissions of elements in some figures are not necessarily indicative of the presence or absence of particular elements in any of the exemplary embodiments, except as may be explicitly delineated in the corresponding written description. None of the drawings are necessarily to scale.

DETAILED DESCRIPTION OF VARIOUS EMBODIMENTS

Although the following text sets forth a detailed description of different embodiments of the invention, it should be understood that the legal scope of the invention is defined by the words of the claims set forth at the end of this patent. The detailed description is to be construed as exemplary only and does not describe every possible embodiment of the invention since describing every possible embodiment would be impractical, if not impossible. Numerous alternative embodiments could be implemented, using either current technology or technology developed after the filing date of this patent, which would still fall within the scope of the claims defining the invention.

It should also be understood that, unless a term is expressly defined in this patent using the sentence "As used herein, the term '_____' is hereby defined to mean . . ." or a similar sentence, there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims at the end of this patent is referred to in this patent in a manner consistent with a single meaning, that is done for sake of clarity only so as to not confuse the reader, and it is not intended that such claim term be limited, by implication or otherwise, to that single meaning. Finally, unless a claim element is defined by reciting the word "means" and a function without the recital of any structure, it is not intended that the scope of any claim element be interpreted based on the application of 35 U.S.C. §112, sixth paragraph According to the present disclosure, a pharmaceutical product is disclosed. The pharmaceutical product comprises a container with a layer of nickel or nickel alloy, the layer facing the interior of the container. The container may be in the form of a bottle or a drum, for example. The container may be sealed to limit the escape of or access to the anesthetic in the receptacle, and may include a cap, a valve assembly or other device to this end. The receptacle may hold a halogenated anesthetic, such as sevoflurane (fluoromethyl 2,2,2-trifluoro-1-[trifluoromethyl]ethyl ether), desflurane (1,2,2,2-tetrafluoroethyl difluoromethyl ether), isoflurane (1-chloro-2,2,2-trifluoroethyl difluoromethyl ether), enflurane (2-chloro-1,1,2-trifluoroethyl-difluoromethyl ether), methoxyflurane (2,2-dichloro-1,1-difluoroethyl methyl ether) and halothane (2-bromo-2-chloro-1,1,1-trifluoroethane), which may be disposed in the interior the receptacle. According to certain embodiments, the receptacle may hold a halogenated anesthetic selected from the group consisting of sevoflurane, desflurane, isoflurane, enflurane, methoxyflurane and halothane. All of these halogenated anesthetics may be liquids under ambient conditions.

Figure 1:
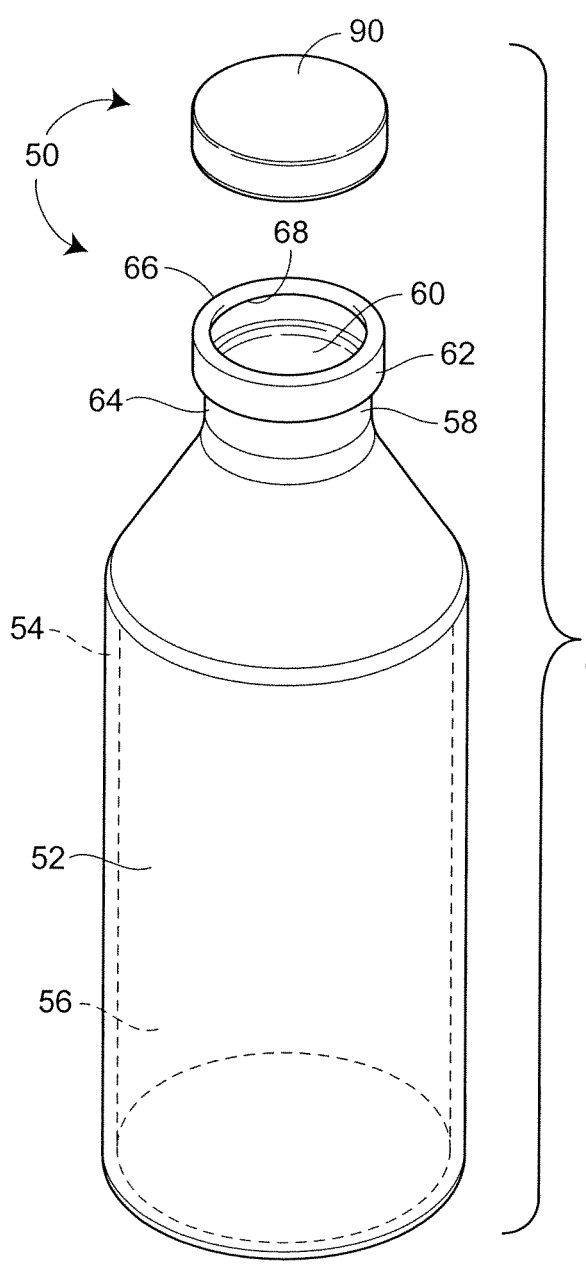
FIG. 1 is a perspective view of a container according to the present disclosure.

FIG. 1 illustrates an embodiment of an anesthetic container 50 for use in the above-mentioned pharmaceutical product. This is an exemplary form for the container 50, and is not intended to limit the scope of the disclosure thereto. As noted above, the container may take other forms than that illustrated in FIG. 1, such as a drum or the like.

The illustrated container 50 includes a receptacle 52, in the form of a bottle, with a wall 54 that defines an interior 56. According to the illustrated embodiment, the wall 54 also defines a neck 58 with a passage 60 in fluid communication with the interior 56. As illustrated in FIG. 1, the embodiment of the bottle-shaped receptacle 52 has a neck 58 with a smaller cross-section than the widest part of the receptacle 52; this need not be the case according to all embodiments of the present disclosure. In addition, the receptacle 52 has a flange 62, which may be positioned at the neck 58 of the receptacle 52. As illustrated in FIG. 1, the flange 62 may depend from an outer surface 64 of the wall 54 to define a rim 66 about an opening 68 in communication with the passage 60 through the neck 58.

Figure 2:
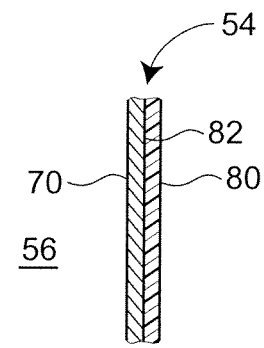
FIG. 2 is a partial cross-sectional view of the wall of the receptacle of FIG. 1.
Figure 3:
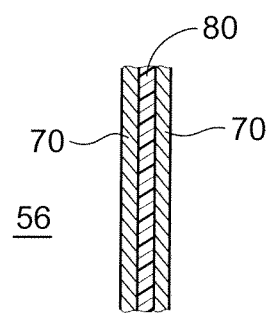
FIG. 3 is a partial cross-sectional view of the wall of the receptacle of FIG. 1 according to another embodiment.

According to the embodiments of the present disclosure, as seen in FIG. 2, the wall 54 may include a layer 70 of nickel or nickel alloy facing the interior 56 of the receptacle 52. According to the illustrated embodiment, the wall 54 may also include a layer 80 of aluminum or aluminum alloy, or some other metal, such as steel. According to the illustrated embodiment, the layer 70 may be disposed on a surface 82 of the layer 80 facing the interior 56 of the receptacle 52. According to certain embodiments, the layer 70 may be disposed on both surfaces of the layer 80. See FIG. 3.

Depending on the embodiment, the layer 70 may be continuous or discontinuous. Where the layer 70 is continuous, the layer 70 may be disposed facing the entire interior 56 of the receptacle 52. Where the layer 70 is discontinuous, the discontinuity of the layer 70 may be the result of a conscious decision to make the layer 70 discontinuous (e.g., a pattern) or as a consequence of process conditions when the layer 70 is formed on the surface 82 (e.g., an incomplete plating). Whether continuous or discontinuous, at least a portion of the layer 70 is in direct contact with the anesthetic disposed inside the receptacle 52.

Where the layer 70 is disposed on a layer 80 to define the wall 54, the layer 70 may be disposed on the layer 80 using conventional plating techniques. Additionally, other materials may be combined with the nickel and/or nickel alloy layer 70. For example, polytetrafluoroethylene (PTFE) may be used in combination with the nickel and/or nickel alloy layer 70. That is, the PTFE may be co-deposited with the nickel or nickel alloy, or the nickel or nickel alloy may be plated and then the PTFE may be infused in the layer 70, for example.

In comparative testing, it has been surprisingly shown that a receptacle having a wall including a layer of nickel disposed on a layer of aluminum has performance characteristics similar to existing technology. In particular, tests were performed on a aluminum receptacle with a layer of nickel facing the interior of the receptacle, and an aluminum receptacle with a layer of epoxy-phenolic resin facing the interior of the receptacle. Both receptacles were filled with sevoflurane and stored at 55 C for a period of approximately one month (44 days for the receptacle with a layer of nickel, one month for the receptacle with a layer of epoxy-phenolic resin). At the end of the period, the sevoflurane was examined visually and certain chemical analyses were performed. The sevoflurane in both containers was clear and colorless, and the pH was approximately the same (5.7 for the sevoflurane from the receptacle with a layer of nickel, and 5.6 for the sevoflurane from the receptacle with layer of epoxy-phenolic resin). Furthermore, using gas chromatography, no semivolatile impurities greater than 0.05 ppm (the lower limit reliably detectable) or greater than the level of semivolatile impurities found in the solvent matrix used (in this case, isooctane) were detected in samples of sevoflurane taken from the two different receptacles. Moreover, again using gas chromatography, the impurities detected in the sevoflurane contained in both receptacles were present in approximately similar amounts (sevoflurane: 99.998 wt. %; total impurities: 0.0016 wt. % for both receptacles). Taken in light of the criticism of the use of nickel with anesthetics, such as sevoflurane, it is believed that the similarity of the test results would not have been expected.

As is also illustrated in FIG. 1, the container 50 includes a closure 90, which closure 90 may be fitted over the opening 68 to prevent the anesthetic from escaping from the receptacle 52. The closure 90 should be chosen so as not to compromise the characteristics of the container 50; the closure 90 may provide structural integrity, inertness and vapor barrier properties. As illustrated, the closure 90 is in the form of a cap. The cap 90 may be attached to the neck 58 of the receptacle 52 through the use of threads formed on the cap 90 and the flange 62. Alternatively, the cap 90 may simply be held in place by a "snap-off" fit.

Figure 4:
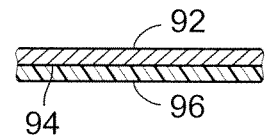
FIG. 4 is a partial cross-sectional view of the closure of FIG. 1.

The closure 90 may be made of aluminum or other metal, or of a polymer material. The closure 90 may be lined, as illustrated in FIG. 4. That is, the closure 90 may have a wall 92 with an inner surface 94 on which a layer 96 of inert lining is disposed. The layer 96 may be an enamel or a lacquer, such as may include an epoxy-phenolic resin, or may include polytetrafluoroethylene (PTFE). One suitable lining is commercially available under the name "Plytrax 100" and has a PTFE facing with a polyethylene foam backing, available from Norton Performance Plastics Corporation, 150 Day Road, Wayne N.J. 07470-4699, a subsidiary of Saint-Gobain Performance Plastics. The layer 96 may also be of nickel or nickel alloy.

The cap 90 illustrated in FIG. 1 is but one exemplary closure that may be included in a container according to the present disclosure. For example, the closure may instead be in the form of a valve assembly, such as is illustrated in U.S. Pat. Nos. 5,505,236 and 5,617,906, for example, the disclosure of these patents being incorporated in their entirety herein. It is also possible to use both a closure in the form of a valve assembly and a closure in the form of a cap in a single embodiment according to the present disclosure, the cap providing a barrier to anesthetic loss as well as limiting access to and contamination of the valve assembly.

In general terms, a suitable valve assembly would alternatively close to minimize loss of anesthetic from the container and open (by way of interaction with the vaporizer port, for example) to permit anesthetic to transfer from the container to another receptacle or a device, such as a vaporizer. Similar to the cap-type closures mentioned above, valve assemblies may be screwed or snapped onto the container, or a crimped ferrule may be used to secure the valve assembly to the receptacle. Alternatively, the valve assembly may be assembled with the receptacle prior to use, but not be permanently secured to the receptacle at the time of manufacture.

While not illustrated, when the container is to be used to supply final product for patient administration, either component of the container (the receptacle or the closure) may be provided with indexing elements that allow the container to mate only with a vaporizer having corresponding indexing elements. This may help to ensure that the anesthetic is administered only through the vaporizer for which it was designed. Along similar lines, the size and shape of the container may be varied to indicate a particular type of inhalation anesthetic to avoid different types of anesthetics being mixed in a vaporizer.

Further, while the illustrated embodiment is of a single-piece, bottle-shaped receptacle, the present disclosure is not so limited. The receptacle may be formed instead as a two-piece, or even a three-piece, receptacle. Further, the receptacle may be in the form of a larger tank or drum for use during shipping, mixing or holding of the inhalation anesthetic in the bulk drug form or in a crude manufactured form awaiting final distillation. It will also be recognized that the container, regardless of its size or shape, may be disposed inside of another container. According to such an embodiment, the container as described above may form of an inner layer disposed within an outer layer, or jacket, of plastic or steel, for example.

As to the use of a pharmaceutical product according to the present disclosure, a method may include obtaining a container including a receptacle having a wall including a layer of nickel or nickel alloy, the layer facing an interior of the receptacle. The method may also include filling the container with a halogenated anesthetic selected from the group consisting of sevoflurane, desflurane, isoflurane, enflurane, methoxyflurane, and halothane. Further, the method may include sealing the container once the filling is complete, with a closure, valve assembly or the like, for example. The method of use may additionally (or alternatively) include dispensing a halogenated anesthetic selected from the group consisting of sevoflurane, desflurane, isoflurane, enflurane, methoxyflurane, and halothane from the container. Such a method may also include unsealing the container prior to dispensing the halogenated anesthetic.

I claim:

1. A pharmaceutical product comprising:
    a long-term storage container comprising a receptacle having a wall including a layer of nickel or nickel alloy, the layer facing an interior of the receptacle; and
    a halogenated anesthetic selected from the group consisting of sevoflurane, desflurane, isoflurane, enflurane, methoxyflurane and halothane disposed within the container, the container capable of storing the halogenated anesthetic for at least one month, wherein the receptacle is in the form of a bottle.

2. The pharmaceutical product according to claim 1, the wall including aluminum or aluminum alloy.

3. The pharmaceutical product according to claim 2, wherein the layer is plated onto the aluminum or aluminum alloy.

4. The pharmaceutical product according to claim 1, wherein the layer is continuous.

5. The pharmaceutical product according to claim 1, wherein the layer is discontinuous.

6. The pharmaceutical product according to claim 1, wherein the layer comprises polytetrafluoroethylene.

7. The pharmaceutical product according to claim 1, wherein the container comprises a closure.

8. The pharmaceutical product according to claim 7, wherein the closure comprises a cap.

9. The pharmaceutical product according to claim 8, wherein the closure has a layer of inert lining disposed thereon.

10. The pharmaceutical product according to claim 9, wherein the layer disposed on the closure comprises polytetrafluoroethylene.

11. The pharmaceutical product according to claim 1, wherein the halogenated anesthetic has semivolatile impurities of no greater than 0.05 ppm after storing the halogenated anesthetic in the container for about one month.

12. A method of use of a pharmaceutical product, the method comprising:
    obtaining a long-term storage container including a receptacle having a wall including a layer of nickel or nickel alloy, the layer facing an interior of the receptacle;
    filling the container with a halogenated anesthetic selected from the group consisting of sevoflurane, desflurane, isoflurane, enflurane, methoxyflurane, and halothane; and
    storing the halogenated anesthetic in the storage container for at least one month.

13. The method according to claim 12, further comprising sealing the container once the filling is complete.

14. The method according to claim 12, further comprising dispensing the halogenated anesthetic selected from the group consisting of sevoflurane, desflurane, isoflurane, enflurane, methoxyflurane, and halothane from the container.

15. The method according to claim 14, further comprising unsealing the container prior to dispensing the halogenated anesthetic.

16. The method according to claim 12, wherein the halogenated anesthetic has semivolatile impurities of no greater than 0.05 ppm after storing the halogenated anesthetic in the container for about one month.

17. A pharmaceutical product comprising:
a long-term storage container comprising a receptacle having a wall including a layer of nickel or nickel alloy, the layer facing an interior of the receptacle; and
a halogenated anesthetic selected from the group consisting of sevoflurane, desflurane, isoflurane, enflurane, methoxyflurane and halothane disposed within the container, the container capable of storing the halogenated anesthetic for at least one month, wherein the halogenated anesthetic has semivolatile impurities of no greater than 0.05 ppm after storing the halogenated anesthetic in the container for about one month.

18. The pharmaceutical product according to claim 17, the wall including aluminum or aluminum alloy.

19. The pharmaceutical product according to claim 18, wherein the layer is plated onto the aluminum or aluminum alloy.

20. The pharmaceutical product according to claim 17, wherein the container comprises a closure.

\* \* \* \* \*